United States Patent
Fryer

(10) Patent No.: US 12,161,770 B2
(45) Date of Patent: Dec. 10, 2024

(54) LOAD VOLUME DETERMINATION METHOD FOR A STERILIZATION APPARATUS

(71) Applicant: Advanced Sterilization Products, Inc., Irvine, CA (US)

(72) Inventor: Benjamin M. Fryer, Lake Forest, CA (US)

(73) Assignee: Advanced Sterilization Products, Inc., Irvine, CA (US)

( * ) Notice: Subject to any disclaimer, the term of this patent is extended or adjusted under 35 U.S.C. 154(b) by 699 days.

(21) Appl. No.: 17/442,936

(22) PCT Filed: Mar. 25, 2020

(86) PCT No.: PCT/IB2020/052827
§ 371 (c)(1),
(2) Date: Sep. 24, 2021

(87) PCT Pub. No.: WO2020/201932
PCT Pub. Date: Oct. 8, 2020

(65) Prior Publication Data
US 2022/0175994 A1  Jun. 9, 2022

Related U.S. Application Data

(60) Provisional application No. 62/826,695, filed on Mar. 29, 2019.

(51) Int. Cl.
*A61L 2/24* (2006.01)
*A61L 2/20* (2006.01)
(Continued)

(52) U.S. Cl.
CPC ............... *A61L 2/208* (2013.01); *A61L 2/26* (2013.01); *G01F 17/00* (2013.01);
(Continued)

(58) Field of Classification Search
CPC ............... G01F 17/00; A61L 2/24; A61L 2/26
See application file for complete search history.

(56) References Cited

U.S. PATENT DOCUMENTS

| 4,203,943 A | 5/1980 | Gillis et al. |
| 4,744,951 A | 5/1988 | Cummings et al. |

(Continued)

FOREIGN PATENT DOCUMENTS

| CA | 2 299 914 A1 | 9/2000 |
| CA | 2 376 117 A1 | 12/2000 |

(Continued)

OTHER PUBLICATIONS

PCT Written Opinion of the International Searching Authority of PCT/IB2020/052827 dated Jul. 1, 2020, 4 pages.
(Continued)

*Primary Examiner* — Kevin Joyner
(74) *Attorney, Agent, or Firm* — Lerner David LLP

(57) ABSTRACT

A method to improve efficiency of operating a sterilizer is disclosed. The method includes determining a volume of a load inside the sterilizer based on pressure measurements as a function of time. The determined volume may be used to decide whether to conduct a sterilization procedure. If the sterilization procedure is to be conducted, the volume data may be used to estimate the duration of the procedure, which duration may be communicated to a user.

20 Claims, 2 Drawing Sheets

(51) Int. Cl.
*A61L 2/26* (2006.01)
*G01F 17/00* (2006.01)

(52) U.S. Cl.
CPC ... *A61L 2202/121* (2013.01); *A61L 2202/122* (2013.01); *A61L 2202/14* (2013.01); *A61L 2202/24* (2013.01)

(56) References Cited

U.S. PATENT DOCUMENTS

| | | |
|---|---|---|
| 4,956,145 A | 9/1990 | Cummings et al. |
| 5,527,508 A | 6/1996 | Childers et al. |
| 5,804,139 A | 9/1998 | Lin et al. |
| 5,851,458 A | 12/1998 | DeVos et al. |
| 5,955,025 A | 9/1999 | Barrett |
| 5,961,922 A | 10/1999 | Witte et al. |
| 6,106,772 A | 8/2000 | Kohler et al. |
| 6,218,189 B1 | 4/2001 | Antonoplos et al. |
| 6,325,972 B1 | 12/2001 | Jacobs et al. |
| 6,333,002 B1 | 12/2001 | Jacobs et al. |
| 6,451,254 B1 | 9/2002 | Wang et al. |
| 6,656,426 B1 | 12/2003 | Wang et al. |
| 6,852,279 B2 | 2/2005 | Williams et al. |
| 7,161,677 B2 | 1/2007 | Kawasaki |
| 7,201,869 B2 | 4/2007 | Williams et al. |
| 7,670,550 B2 | 3/2010 | Lin et al. |
| 7,807,100 B2 | 10/2010 | Choperena et al. |
| 9,101,679 B2 | 8/2015 | Robitaille et al. |
| 10,111,975 B2 | 10/2018 | Laflamme et al. |
| 2002/0044883 A1 | 4/2002 | Jacobs et al. |
| 2003/0156977 A1 | 8/2003 | Kohler et al. |
| 2006/0185189 A1 | 8/2006 | Kawasaki |
| 2007/0269339 A1 | 11/2007 | Frost |
| 2009/0060781 A1 | 3/2009 | Adams |
| 2010/0313441 A1 | 12/2010 | McLaren et al. |
| 2011/0070124 A1 | 3/2011 | Lewis |
| 2011/0076192 A1 | 3/2011 | Robitaille et al. |
| 2013/0243649 A1 | 9/2013 | Dufresne et al. |
| 2015/0313250 A1 | 11/2015 | Itarashiki et al. |
| 2016/0310622 A1 | 10/2016 | Goetz et al. |
| 2018/0207306 A1 | 7/2018 | Olson et al. |

FOREIGN PATENT DOCUMENTS

| | | |
|---|---|---|
| CA | 2 528 333 A1 | 1/2005 |
| EP | 1 378 248 A1 | 1/2004 |
| GB | 2 388 545 A | 11/2003 |
| JP | S57-142254 A | 9/1982 |
| JP | 2000-217894 A | 8/2000 |
| JP | 2002-090296 A | 3/2002 |
| WO | 01/21223 A1 | 3/2001 |
| WO | 01/70282 A1 | 9/2001 |
| WO | 2004/054883 A1 | 7/2004 |
| WO | 2007/012866 A1 | 2/2007 |

OTHER PUBLICATIONS

PCT International Search Report of PCT/IB2020/052827 dated Jul. 1, 2020, 3 pages.
PCT International Preliminary Report on Patentability of PCT/IB2020/052827 dated Sep. 28, 2021, 5 pages.
Steve Hansen, "Leaks: The Good, the Bad and the Ugly; What leaks are, how to classify and size them, and how to make useful leaks", from the Bell Jar, vol. 7, No. 1, Winter 1998, pp. 1-8, 8 pages.
Sterizone VP4 Sterilizer, Technical Monograph—US Claims only, 205-2016 TSO3, 29 pages.
Australian Patent Application No. 2014317768, Examination Report dated May 26, 2018, 3 pages.

LOAD VOLUME DETERMINATION METHOD FOR A STERILIZATION APPARATUS

CROSS-REFERENCE TO RELATED APPLICATIONS

The present application is a U.S. National Phase Application of International Application No. PCT/IB2020/052827, filed Mar. 25, 2020, which claims priority to U.S. Provisional Patent Application No. 62/826,695, filed Mar. 29, 2019. The entire contents of these applications are incorporated by reference herein in their entirety.

FIELD

The subject matter disclosed herein relates to sterilization of instruments in a vacuum chamber using a gaseous sterilant.

BACKGROUND

Medical devices or instruments are typically sterilized before use to minimize the likelihood that a contaminated device might be used on a subject, which could cause an infection in the subject. Various sterilization techniques may be employed using various sterilants, such as steam, hydrogen peroxide, and vapor phase sterilization, either with or without a gas plasma, and ethylene oxide (EtO).

Certain sterilization techniques are conducted at pressures other than ambient pressure or atmospheric pressure. For example the STERRAD® System, STERRAD® NX System or STERRAD® 100NX System of Advanced Sterilization Products ("ASP"), Division of Ethicon US, LLC, a Johnson & Johnson company, are examples of sterilization systems, or sterilizers, that include a vacuum chamber and operate at low pressures, e.g., less than 200 millitorr, which helps to vaporize hydrogen peroxide injected into the vacuum chamber as a liquid, to maintain hydrogen peroxide in gaseous form, and to avoid condensation of this sterilant onto the instruments being sterilized. Various sterilizers, e.g. the aforementioned STERRAD® systems, are capable of monitoring various process parameters to determine that process goals and thresholds are satisfied to help ensure that medical devices are sterilized or to notify personnel of a process error, which may indicate that the instruments have not been sterilized. One process parameter is the volumetric concentration of a sterilant, e.g., hydrogen peroxide, in the vacuum chamber. These systems each monitor the concentration of hydrogen peroxide to ensure that a minimum concentration is achieved over time. Specifically, the STERRAD® systems monitor the concentration of hydrogen peroxide as a function of time, and when the integral of this concentration with respect to time, sometimes referred to as the Area Under the Curve, or AUC, surpasses a predetermined threshold, the sterilization process may continue. However, if this AUC threshold is not met, the system may abort the process.

When the AUC threshold is not met, condensation of the hydrogen peroxide may be the cause. Various factors may contribute to condensation of the hydrogen peroxide, including available volume in the chamber (i.e., the volume not occupied by the instruments) and the temperature of the instruments. That is, if the instruments occupy a substantial portion of the chamber, the temperature of the instruments is too low, or a combination thereof, the hydrogen peroxide vapor may condense. As such, the STERRAD® systems check to ensure that a minimum AUC threshold is achieved, which provides an assurance that condensation did not substantially occur and that sterilization procedure was efficacious (i.e., that the instruments were sterilized).

SUMMARY OF THE DISCLOSURE

Disclosed herein is a method of operating a sterilizer, comprising placing a load in an unsterile state into a chamber of the sterilizer, lowering a pressure in the chamber to a first pressure, raising the pressure in the chamber from the first pressure to a second pressure, determining a duration during which the pressure in chamber increased from the first pressure to the second pressure, comparing the duration to information that correlates time data to volume data (e.g., a lookup table or a function of best fit), and determining a volume of the load. The method may further include a step of comparing the volume of the load to a threshold volume. Further, the threshold volume may correspond to a challenge-load volume. As such, the method may further comprise determining that the volume of the load is greater than the threshold volume, in which case a determination to avoid sterilizing the load may be made. Thus, the chamber may be open and the load removed from the chamber in the unsterile state. Alternatively, the method may include determining that the volume of the load is less than the threshold volume. As such, the method may further comprise comparing the volume to information that correlates load-volume data to procedure-duration data. Thus, a procedure duration may be determined before commencing a sterilization cycle and the procedure duration may be communicated to a user, e.g., displayed on a display of the sterilizer before commencing the sterilization cycle. Then, for example, thereafter the sterilization cycle may be commenced. During the cycle, particularly after a transfer phase of a sterilant, e.g., hydrogen peroxide, has been completed, a duration for the remainder of the cycle may be determined and communicated to a user.

A sterilizer suitable for conducting this method is also disclosed. The sterilizer may comprise a chamber adapted to maintain a load of instruments, a vacuum pump connected to the chamber and configured to lower a pressure in the chamber to a first pressure, a vent valve connecting the chamber to an exterior of the sterilizer, a non-transitory storage medium in which is stored information that correlates time-data to volume data, a processor configured to access the storage medium, determine a duration during which the pressure in the chamber increases from the first pressure to a second pressure, compare the duration to the information that correlates time data to volume data, and determine a volume of the load.

A threshold volume may be stored in the storage medium. Further, the processor may be configured to compare the volume of the load to the threshold volume, which may correspond to a challenge-load volume. Additionally, information that correlates load-volume data to procedure-duration data may be stored in the storage medium such that the processor may be further configured to determine a procedure duration by comparing the volume information to the information that correlates load-volume data to procedure-duration data.

The processor may be further configured to communicate the procedure duration via a user interface, e.g., a display. The sterilizer may also comprise a source of sterilant, e.g., hydrogen peroxide.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
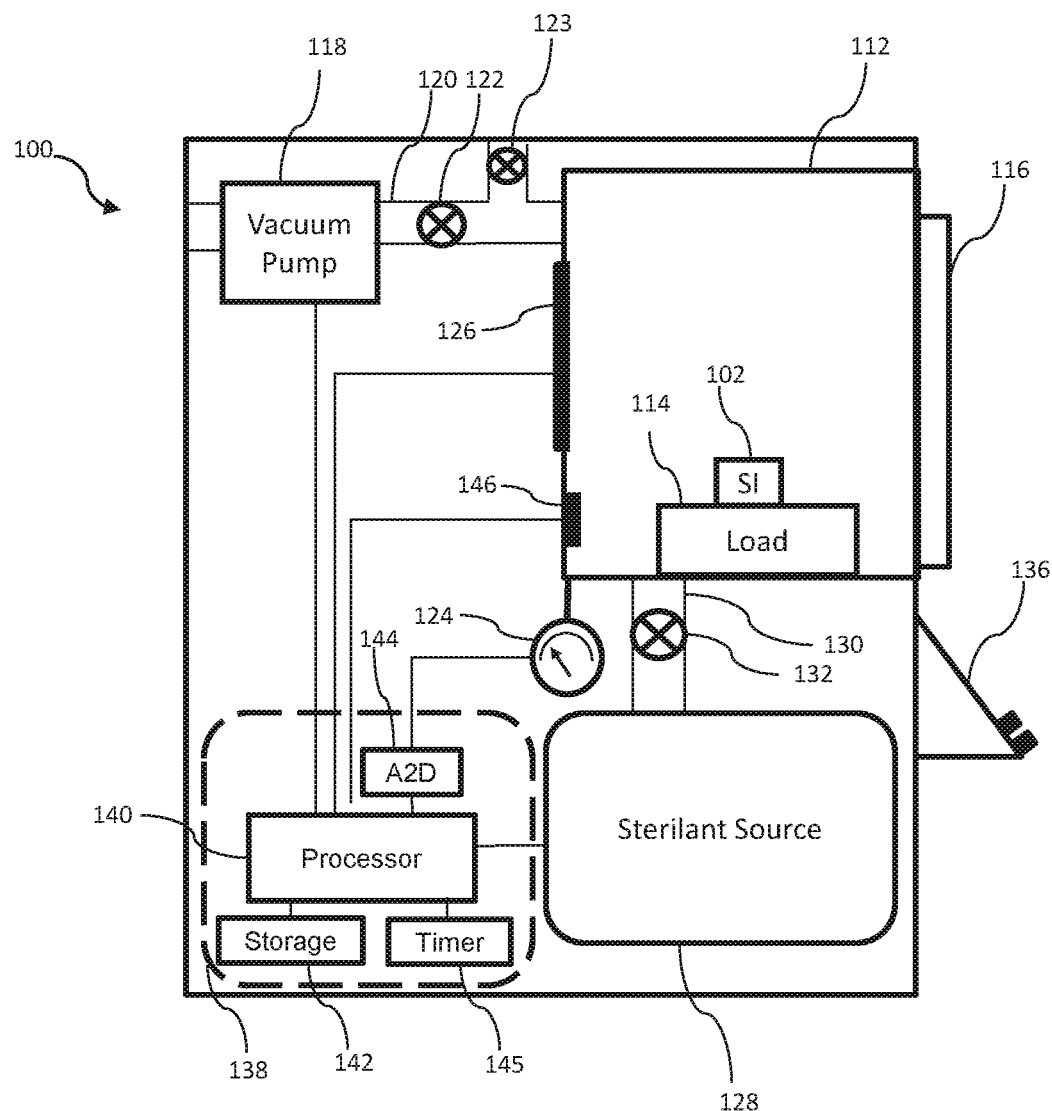
FIG. 1 depicts a schematic representation of a sterilizer.

A schematic representation of a sterilizer 100, e.g., the STERRAD® 100NX System, is reflected in FIG. 1. Sterilizer 100 comprises a vacuum chamber 112, which is configured to maintain a load (pack) 114 of instruments therein to be sterilized. One or more sterilization indicators (e.g., a biological indicator 102) may be disposed within chamber 112, such as placed upon or secured to load 114 as shown. The chamber 112 may be formed of any material that is sufficiently robust to handle pressures as low as approximately between 0.3 torr and 3 torr, and sufficiently inert to avoid reacting with or absorbing any sterilants introduced therein. Such materials may include aluminum and stainless steel Chamber 112 may also include an openable and sealable barrier 116, such as a door, that may be opened to allow placement and removal of load 114 into chamber 112. The barrier should be sufficiently robust, and include a sufficiently robust seal, to withstand low pressures in chamber 112 and avoid leaks between chamber 112 and the ambient environment. A vacuum pump 118 capable of reaching the desired operating pressure evacuates air and other gases, such as water vapor, from chamber 112. Vacuum pump 118 may include a hose or pipe 120 to connect it to chamber 112. Vacuum pump 118 may also include a valve 122, which may be open or closed to assist or prevent pressure changes in chamber 112. For example, when the valve is open and the vacuum pump is operational, the pressure in chamber 112 may be lowered. Alternatively, when the valve is open and the vacuum pump is not operational, pressure in the chamber may be increased toward or equalized to the ambient pressure such that valve 122 may be considered a vent valve. In other embodiments, another vent valve 123 may be used to vent chamber 112. A pressure monitor or transducer 124 measures the pressure in chamber 112. Particularly suitable pressure monitors are capacitance manometers available from MKS Instruments. A heating element 126 may be used to heat the chamber 112. It may comprise separate elements bonded to the outside of the chamber 112 in locations sufficient to uniformly heat the chamber 112. A source of sterilant 128, e.g., a reservoir or a cartridge containing the sterilant, which may additionally include or be connected to a hose or pipe 130, is connected to chamber 112. In some embodiments, reservoir 128 may further include or be connected to a valve 132, which may be disposed between chamber 112 and source 128 to control the flow of sterilant from source 128 through hose 130 and into chamber 112. Sterilization system 100 may also comprise a user interface 136, which may further include output devices, such as a printer, display, and alarm. User interface 136 may also include input devices, such as a keypad or touch screen. Finally, system 100 may also comprise a hydrogen peroxide monitor 146 capable of monitoring and outputting hydrogen peroxide data.

A control system 138, such as a digital computer, controls the operation of sterilizer 100 and its various components. Control system 138 may employ one or more microprocessors 140. It may also employ a non-transitory storage medium 142, such as random access memory (RAM), a hard-disk drive, or flash memory, which can store, e.g., information and data. An analog to digital (A2D) converter 144 may be used to convert analog data to digital data if analog data, such as pressure data or hydrogen peroxide concentration, is collected. A timer or clock circuit 145 keeps time. Control system 138 may further include software and/or logic by which microprocessor 140 may determine the volume of load 114 and the amount of time, or approximately the amount of time, needed to reach the threshold AUC, e.g., based on the volume of load 114. Processor 140 may be configured to automatically end a sterilization process upon determining, e.g., that the volume of load 114 is greater than a threshold volume, that the AUC threshold has been met, or that the AUC threshold has not been met within a certain amount of time. For clarity, certain connections between processor 140 and other components of sterilizer 100 are not shown. However, it should be understood that sterilizer 100 is configured such that processor 140 may control all functions of sterilizer 100.

Determination by sterilizer 100, i.e., by control system 138 and processor 140, of the volume of load 114 may be useful for at least two reasons. First, if the volume of load 114 is too large relative to the volume of vacuum chamber 112, the gaseous hydrogen peroxide within chamber 112 may condense and prevent the threshold AUC from being reached. In these instances, processor 140 could alert healthcare personnel of the issue via user interface 136, and, in some configurations, also prevent a sterilization procedure from being conducted on the load. Second, where the volume of load 114 is not too large, the volume of the load may be used by processor 140 to determine the amount of time, or approximate amount of time, necessary to reach the threshold AUC in chamber 212, such that processor 140 could alert healthcare personnel via user interface 136 of the amount of time the sterilization process is expected to last. Accordingly, time savings may be achieved and alerted to healthcare personnel early in the sterilization process such that healthcare personnel may prepare for and utilize the time savings in an expeditious manner.

Determination of the volume of load 114 within chamber 112 may be determined by use of the following equation:

$$Q = V\frac{\Delta P}{\Delta t}$$

where Q is the throughput, i.e., number of standard condition volume units that flow in a given period of time through the vent valve (e.g., valve 122, 123, or both), V is the volume of chamber 112 or the volume of chamber 112 not occupied by load 114, $\Delta t$ is the measurement period, and $\Delta P$ is the pressure change during the measurement period. Additional information concerning this equation is available in Steve Hansen, "Leaks: The Good, the Bad and the Ugly," 7 *Bell Jar* 1 (1998).

As relevant to the present disclosed subject matter, first, the throughput, Q, may be determined for an empty chamber of a known volume by fixing $\Delta P$ as some pressure interval where pressure transducer 124 may measure accurately and the pressure rise is linear or substantially linear. For example, in the STERRAD® 100NX system, the volume of chamber 112 is approximately 152 liters and transducer 124 measures pressure accurately, i.e., to about 0.001 torr, from approximately 20 torr to approximately 600 torr. Applicant conducted trials in the STERRAD® 100NX system during which chamber 112 was pumped down to a lower test pressure of 20 torr. Subsequently, chamber 112 was vented to the environment until the pressure in chamber 112 increased to an upper test pressure of 600 torr. Time and pressure data were collected while the chamber was vented from the lower test pressure to the upper test pressure. From this data, an average Q through the vent valve was calculated using the above equation as approximately 6101 torr*liter/second. Knowing Q for the system, Applicant then conducted additional trials with various loads contained in chamber 112. Such loads occupied approximately four liters, approximately nineteen liters, and approximately thirty liters. Again, chamber 112 was pumped down to approximately 20 torr and vented. Time and pressure data were again collected from approximately 20 torr and 600 torr. From this data, Applicant observed that, relative to the empty chamber, the vent time for the approximately four liter volume was reduced by approximately one second, the vent time for the approximately nineteen liters was reduced by approximately two seconds, and the vent time for the approximately thirty liters was reduced by approximately four seconds.

Based on this data as well as additional data concerning other load volumes, information correlating time data to load-volume data, e.g., a lookup table or a function of best fit, may be generated and stored in storage medium 142 such that processor 140 may determine the volume of load 114 based on the amount of time needed to raise the pressure in chamber 112 from a first pressure to a second pressure. Although Applicant used values of 20 torr for the lower test pressure and 600 torr for the upper test pressure, other pressures values may be used, e.g., between approximately 5 torr and approximately 30 torr for the lower test pressure and between approximately 500 torr to approximately 700 torr for the upper test pressure. Whatever the test pressures may be, the key is to determine the time it takes to vent chamber 112 from the lower test pressure to the upper test pressure, such that the average Q may be determined for a given sterilizer 100 and such that data may be generated to create information, e.g., a lookup table or function of best fit correlating vent time to load volume, that may be used in subsequent load determination methods described below.

This information may also include a threshold volume, e.g., corresponding to a so-called "challenge" load (described below), below which a threshold AUC may be achieved and above which the threshold AUC may not be achieved. This information may optionally also include temperature information to further refine the accuracy with which the processor may correctly predict the likelihood that the AUC may or may not be reached. For example, predetermined combinations of volume load and volume temperature (see Table 1, below) may be correlated to success and failure to reach the threshold AUC and stored in storage medium 142, e.g., included in the aforementioned lookup table or provided in a separate lookup table also stored in storage medium 142. In those embodiments where temperature is accounted for, temperature may be monitored by, e.g., placing a thermocouple on the load and connecting it to processor 140, storage medium 142, or both, to provide temperature data of the load to processor 140. Alternatively, the user may measure the temperature of the load before placing the load into chamber 112, e.g., by using thermocouple or a touch-free infrared thermometer.

After the volume and optionally the temperature of load 114 are determined, processor 140 may determine whether or not the threshold AUC may be achieved with reference to information stored in storage medium 142, such as the threshold volume described in the preceding paragraph. If processor 140 determines that the AUC may not be achieved, processor 140 may alert healthcare personnel via user interface 136 and, optionally, prevent a sterilization procedure form being commenced upon the load. If processor 140 determines that the AUC may be achieved, processor 140 may determine a duration of the sterilization procedure and alert healthcare personnel of this duration before the sterilization procedure commences.

With continuing reference to the STERRAD® 100NX system, this system is capable of performing sterilization procedures under various process parameters, which healthcare personal may select based on various characteristics of the load, such as if the load might include single-channel flexible endoscopes, flexible endoscopes with cameras, or rechargeable batteries. Most surgical instruments sterilized in the STERRAD® 100NX system are sterilized using the system's Standard Cycle, which lasts approximately forty-seven minutes. The Standard Cycle comprises two half cycles, each of which includes various phases, such as a pump-down phase, a sterilant (hydrogen peroxide) transfer phase, and a plasma phase. In the hydrogen peroxide transfer phases, each of which may be referred to as a transfer phase, hydrogen peroxide begins to be pumped into chamber 112, typically when the pressure in chamber 112 is approximately three torr. Continued introduction of hydrogen peroxide into chamber 112 causes the pressure and the concentration of hydrogen peroxide in the chamber to increase. In the commercially available version of the STERRAD® 100NX, 5.5 ml of liquid hydrogen peroxide is pumped into chamber 112 over approximately eight minutes. The liquid hydrogen peroxide changes phase to gaseous form due to the low pressure in the chamber. The eight minute duration is fixed in the commercially available version of the STERRAD® 100NX based on determinations made by Applicant corresponding to so-called "challenge" loads having large volumes (e.g., greater than or equal to about 5.2 liters) and cold temperatures (e.g., cooler than about 5° C.), referred to herein as challenge-load volumes and challenge-load temperatures. Applicant has determined that within 8 minutes, an AUC of at least 747 mg-sec/L is achieved, which corresponds to a sufficient concentration of hydrogen peroxide being in chamber 112 for a sufficient amount of time to sterilize the challenge loads. However, many loads sterilized in Applicant's commercially available systems have a smaller volume than the challenge-load volume and are warmer than the challenge-load temperature. As such, for these loads, the AUC is commonly achieved in less than eight minutes but the transfer phase nonetheless continues for eight minutes.

This scenario presents an opportunity to save time and hydrogen peroxide. Specifically, a sterilization system may be configured to terminate the transfer phase upon determining that a predetermined AUC threshold (e.g., approximately 747 mg-sec/L) has been satisfied. To maximize the value of these prospective time savings to healthcare personnel and their healthcare facility, it is beneficial to communicate the time savings to healthcare personnel before or early in the sterilization process.

Applicant conducted various trials to determine the amount of time required to achieve the predetermined AUC threshold of approximately 747 mg-sec/L during the transfer phase in the STERRAD® 100NX system for loads that are smaller, warmer, or smaller and warmer than the challenge loads. Exemplary data from these trials are presented in Table 1. Loads having volumes and temperatures such as those reported in Table 1 are often sterilized in sterilizers such as the STERRAD® 100NX system.

TABLE 1

| Load volume (L) | Load Temperature (C.) | Time to reach AUC in transfer phase (mins) | Procedure duration (mins) |
| --- | --- | --- | --- |
| 5.220 | 18 | 6.28 | 43.6 |
|  | 25 | 4.82 | 40.6 |
|  | 35 | 3.38 | 37.8 |
| 5.067 | 18 | 6.8 | 44.6 |
|  | 25 | 4.82 | 40.6 |
|  | 35 | 3.35 | 37.7 |
| 2.732 | 18 | 5.4 | 41.8 |
|  | 25 | 3.83 | 38.7 |
|  | 35 | 2.87 | 36.7 |
| 2.213 | 18 | 4.83 | 40.7 |
|  | 25 | 3.3 | 37.6 |
|  | 35 | 2.85 | 36.7 |

Because the transfer phase in the commercially available STERRAD® 100NX lasts approximately eight minutes, and because two transfer phases are performed during the Standard Cycle, overall time savings in the Standard Cycle may be calculated as twice the difference between the eight minutes and the time to reach the AUC reported in table 1. As such, the current overall procedure duration of 47 minutes may be reduced by this amount, as also reported in Table 1. Notably, the reported trials lasted for a procedure duration of substantially less time than the current 47 minutes. The time savings may be even greater for less challenging loads, e.g., warm loads (approximately 35° C.) that are less than 2.2 liters.

Based on the foregoing, information, e.g., a lookup table or function of best fit, correlating load volume and optionally temperature to procedure durations may be input into and stored in storage medium 142. Accordingly, upon determining the volume of the load, e.g., in the manner described above, and optionally the temperature, processor 140 may determine the expected duration of the overall sterilization process and report it to healthcare personnel via user interface 136.

Figure 2:
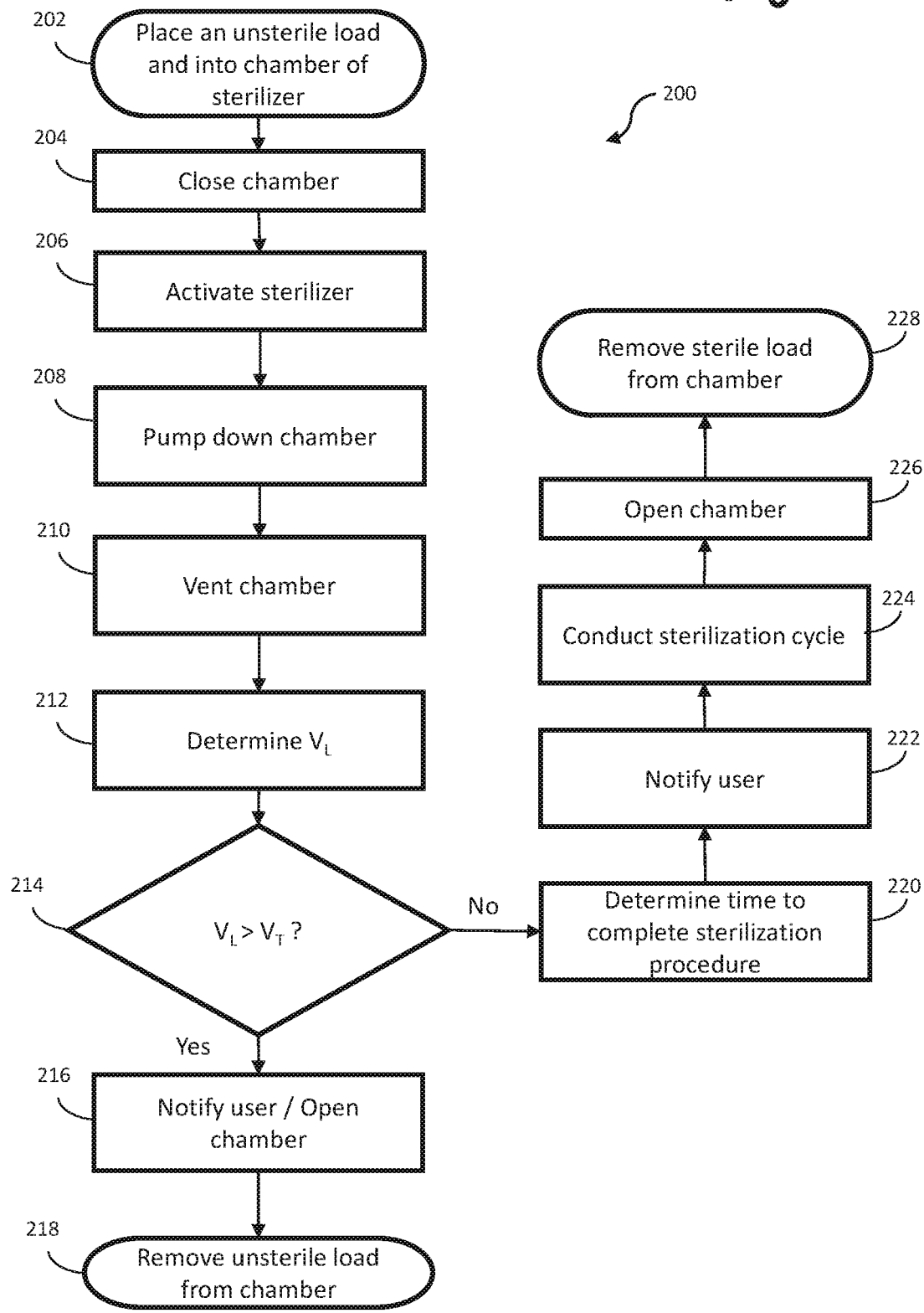
FIG. 2 depicts a flow chart for a method of using the sterilizer.

By virtue of the technology illustrated and described herein, and with reference to FIG. 2, Applicant has devised a method 200 and variations thereof for conducting a sterilization procedure performed by a sterilizer comprising a chamber, e.g., sterilizer 100 of FIG. 1. Method 200 begins at step 202 in which a user of sterilizer 100, e.g., healthcare personnel, places a load 114 including, e.g., a non-sterile medical device or a plurality of non-sterile medical devices, into chamber 112 of sterilizer 100. In step 204 the user closes chamber 112 by shutting door 116. Then, at step 206, the system is activated. Shutting door 116 in step 204 may automatically indicate to processor 140 to activate the system, or the user may activate sterilizer 100 using user interface 136 to inform processor 140 to activate the system. At step 208, processor 140 directs valve 122 to change from a closed configuration to an open configuration and also activates vacuum pump 118. Output from pressure transducer 124 is monitored by processor 140. Vacuum pump 118 continues to operate and lower the pressure in chamber 112 until processor 140 determines that the pressure in chamber 112 has been lowered to a first pressure. Preferably, the first pressure should be equal to or approximately equal to the lower test pressure used in collecting the data used to correlate load volume to vent time as describe above. In that example, the lower test pressure was 20 torr. Upon making this determination, processor 140 deactivates vacuum pump 118 and optionally closes valve 122. Next, at step 210, chamber 210 is vented to the environment such that the pressure in chamber 112 increases to a second pressure. Preferably, the second pressure should be equal to or approximately equal to the upper test pressure used in collecting the data used to correlate load volume to vent time as describe above. In that example, the upper test pressure was 600 torr. In those variations of the method where valve 122 is not closed at the end of pump down step 208, step 210 begins immediately upon deactivation of vacuum pump 118. In those variations of the method where valve 122 is closed at the end of pump down step 208, processor 140 may commence step 210 by either reopening valve 122, opening valve 123, or both. Leaving only pump 123 open in step 210, may assist in increasing the longevity of pump 118, however, it is important that the same valves are open in step 210 as were open when the data used to correlate load volume to vent time was created, otherwise the Q may be different. Processor 140 collects data from pressure transducer 124 and timer 145 throughout step 210 to determine the duration of step 210, i.e., the amount of time to vent chamber from the first pressure to the second pressure, or other pressures therebetween. In step 212, processor 140 compares this data to the information correlating load volume to vent time, e.g., as stored in a lookup table in storage medium 142, to determine $V_L$, the volume of load 114 placed in chamber 112 in step 202. For example, processor 140 may determine that the time required to vent chamber 112 from a first pressure of 20 torr, corresponding to the lower test pressure, to a second pressure of 600 torr, corresponding to the upper test pressure, took approximately the same amount of time it took to vent the chamber when a load having a volume of four liters was disposed in chamber 112. Accordingly, processor 140 may determine that $V_L$ equals approximately four liters.

In step 214, processor 140 checks to determine whether $V_L$ is greater than the threshold volume, $V_T$, which may equal the challenge-load volume described above or otherwise correspond to challenge-load volume (e.g., by equaling the challenge-load volume minus a safety factor, e.g., approximately 5% to approximately 15%, such as approximately 10% of that volume). If $V_L > V_T$, this indicates that sterilizer 100 may be unable to sterilize load 114. In such instances, at step 216, processor 140 notifies the user via user interface 136, by message, alarm, or both, that sterilizer 100 might be unable to sterilize load 114. Preferably, processor 140 also automatically deactivates the system and opens chamber 112 by opening or unlocking door 116. Thus, at step 218, the user may remove the unsterile load from the chamber. Likely, the user would then try to repackage the load into multiple loads, each having a smaller volume than the original load. Alternatively, at step 216, user interface 136 may provide the user with an option to continue with the sterilization procedure at risk that the AUC threshold might not be reached. As such sterilizer 100 may be configured to notify the user if the AUC threshold in actuality is not reached such that the user would understand that the load might remain unsterile. Alternatively, sterilizer 100 may be configured to extend the procedure time or to inject additional hydrogen peroxide to increase the likelihood that the AUC threshold may be reached.

If, however, at step 214, $V_L < V_T$, this indicates that sterilizer 100 should be able to sterilize load 114. As such, at step 220, processor 140 consults the information, e.g., lookup table or function of best fit, in storage medium 142, correlating load volume to procedure duration. As such, processor 140 may determine an amount of time it should take for sterilizer 100 to sterilize load 114. At step 222, processor 140 may notify a user of this predicted time via a display of user interface 136. While this amount of time should be regarded as a prediction, i.e., it may differ somewhat from the actual time to reach the threshold AUC, Applicant has determined that the prediction is fairly accurate such that a user may rely on it in determining how to best use her time (e.g., preparing another load for subsequent sterilization, performing administrative tasks, or taking a break). Optionally, the display may provide a countdown from the predicted time.

Simultaneous with or immediately after step 222, at step 224, processor 140 commences and then conducts the sterilization cycle. During each hydrogen peroxide transfer phase, processor 140 monitors the hydrogen peroxide concentration and terminates the phase upon determining that the threshold AUC has been reached. Accordingly, in certain variations, following a transfer phase, processor 140 may determine the amount of time that a remainder of the cycle should take, i.e., a procedure-remainder duration, and report this to the user via user interface 136.

Upon completing the sterilization cycle, i.e., completing step 224, processor 140 may open chamber 112 by either unlocking or opening door 116. Accordingly, at step 228, the user may remove load 114 in a sterile state from chamber 112.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of operating a sterilizer, comprising:
placing a load in an unsterile state into a chamber of the sterilizer;
lowering a pressure in the chamber to a first pressure;
raising the pressure in the chamber from the first pressure to a second pressure;
determining a duration during which the pressure in the chamber increased from the first pressure to the second pressure;
comparing the duration to information that correlates time data to volume data; and
determining a volume of the load.

2. The method of claim 1, further comprising comparing the volume of the load to a threshold volume.

3. The method of claim 2, wherein the threshold volume corresponds to a challenge-load volume.

4. The method of claim 3, further comprising:
determining that the volume of the load is greater than a threshold volume;
opening the chamber; and
removing the load from the chamber in the unsterile state.

5. The method of claim 3, further comprising determining that the volume of the load is less than a threshold volume.

6. The method of claim 5, further comprising comparing the volume to information that correlates load-volume data to procedure-duration data.

7. The method of claim 6, further comprising determining a procedure duration before commencing a sterilization cycle.

8. The method of claim 7, further comprising displaying the procedure duration on a display of the sterilizer before commencing the sterilization cycle.

9. The method of claim 7, further comprising commencing the sterilization cycle.

10. The method of claim 9, further comprising determining a procedure-remainder duration.

11. The method of claim 10, wherein the step of determining the procedure-remainder duration is performed after a transfer phase of a sterilant.

12. The method of claim 11, wherein the sterilant comprises hydrogen peroxide.

13. The method of claim 7, wherein the information that correlates time data to volume data comprises a first lookup table.

14. The method of claim 7, wherein the information that correlates time data to volume data comprises a first function of best fit.

15. The method of claim 7, wherein the information that correlates volume data to procedure-duration data comprises a second lookup table.

16. The method of claim 7, wherein the information that correlates volume data to procedure-duration data comprises a second function of best fit.

17. A sterilizer, comprising:
a chamber adapted to maintain a load of instruments;

a vacuum pump connected to the chamber and configured to lower a pressure in the chamber to a first pressure;

a vent valve connecting the chamber to an exterior of the sterilizer;

a non-transitory storage medium in which is stored information that correlates time-data to volume data; and a processor configured to
- access the storage medium,
- determine a duration during which the pressure in the chamber increases from the first pressure to a second pressure,
- compare the duration to the information that correlates time data to volume data, and
- determine a volume of the load.

18. The sterilizer of claim 17, wherein a threshold volume is stored in the storage medium and the processor is further configured to compare the volume of the load to the threshold volume.

19. The sterilizer of claim 18, wherein the threshold volume corresponds to a challenge-load volume.

20. The sterilizer of claim 19, wherein information that correlates load-volume data to procedure-duration data is stored in the storage medium and the processor is further configured to determine a procedure duration by comparing the volume information to the information that correlates load-volume data to procedure-duration data.

\* \* \* \* \*